United States Patent [19]

Walton

[11] 4,202,350
[45] May 13, 1980

[54] DEVICE FOR MEASURING PULSE, BREATHING AND RUNNING RATE FOR JOGGERS

[76] Inventor: Charles A. Walton, 20 E. Main St. #33, Los Gatos, Calif. 95030

[21] Appl. No.: 905,774

[22] Filed: May 15, 1978

[51] Int. Cl.² ............................................. A61B 5/02
[52] U.S. Cl. .................... 128/690; 324/78 D
[58] Field of Search .............. 128/2.05 P, 2.05 R, 128/2.05 T, 2.06 F, 2.1 A, 25, DIG. 29, 2.08, 687–690, 680–682, 672–673, 700, 706–707, 722, 748; 73/724; 364/417, 701–703; 324/78 D, 79 D, 103 P, 65; 331/65

[56] References Cited

U.S. PATENT DOCUMENTS

| | | | |
|---|---|---|---|
| 3,324,848 | 6/1967 | Domeier et al. | 128/722 |
| 3,405,288 | 10/1968 | Dittrich | 128/2.05 P |
| 3,675,640 | 7/1972 | Gatts | 128/2.05 R |
| 3,735,387 | 5/1973 | Miller | 324/78 D |
| 3,742,937 | 7/1973 | Manuel et al. | 128/2.05 P X |
| 3,782,368 | 1/1974 | Riebold | 128/DIG. 29 X |
| 3,790,910 | 2/1974 | McCormack | 364/701 |
| 3,797,010 | 3/1974 | Adler et al. | 128/2.1 A X |
| 3,802,698 | 4/1974 | Burian et al. | 128/2.05 P X |
| 3,846,704 | 11/1974 | Bessette | 128/2.05 T X |
| 3,872,455 | 3/1975 | Fuller et al. | 128/2.1 A |
| 3,978,849 | 9/1976 | Geneen | 128/2.05 T |
| 4,026,276 | 5/1977 | Chubbuck | 128/2.05 E X |
| 4,053,755 | 11/1977 | Sherrill | 364/561 |
| 4,112,928 | 9/1978 | Putsch | 128/2.05 R |
| 4,129,125 | 12/1978 | Lester et al. | 128/2.05 R |

*Primary Examiner*—Robert W. Michell
*Assistant Examiner*—Francis J. Jaworski
*Attorney, Agent, or Firm*—Gerald L. Moore

[57] ABSTRACT

A wrist-mounted indicating device coupled to various parts of the body of the wearer for measuring and visually indicating the pulse rate, the breathing rate and the jogging rate during a running exercise.

3 Claims, 10 Drawing Figures

DEVICE FOR MEASURING PULSE, BREATHING AND RUNNING RATE FOR JOGGERS

BACKGROUND OF THE INVENTION

For physical exercise many people have taken up jogging or walking. However for such exercise to be effective it is recommended the heart rate be accelerated to approximately 150 beats per minute or more for healthy persons and be maintained for a minimum period of time each day. In addition, it is beneficial to establish a competitiveness in such exercise. For instance if the runner can compare his present exercise rate or pulse rate with previous measurements, a sense of progress is gained even if the exercise is done alone. Further, for a given running rate, a low pulse rate is a sign of good health.

For persons who have heart problems, it usually is recommended that exercise be in moderation. Instructions from the doctors might dictate that the pulse rate should or should not exceed a predetermined value and extend longer or not longer than a predetermined time period. However presently available systems do not permit the accurate measurement of the pulse rate or give the person a satisfactory indication of the degree to which he is exercising. It is the purpose of the present invention to provide an effective device which can be worn to inform the exerciser continually of the rate at which he is exercising.

SUMMARY OF THE INVENTION

An indicating device for wearing on the wrist to inform the wearer of the body conditions most affected by exercise. The device incorporates sensors positioned on parts of the body for detecting the pulse rate, the breathing rate and the pacing rate of the exerciser. A visual readout is provided for continually indicating these body conditions and the time so the effect of the exercise on the body can be monitored.

DESCRIPTION OF THE INVENTION

Figure 1:
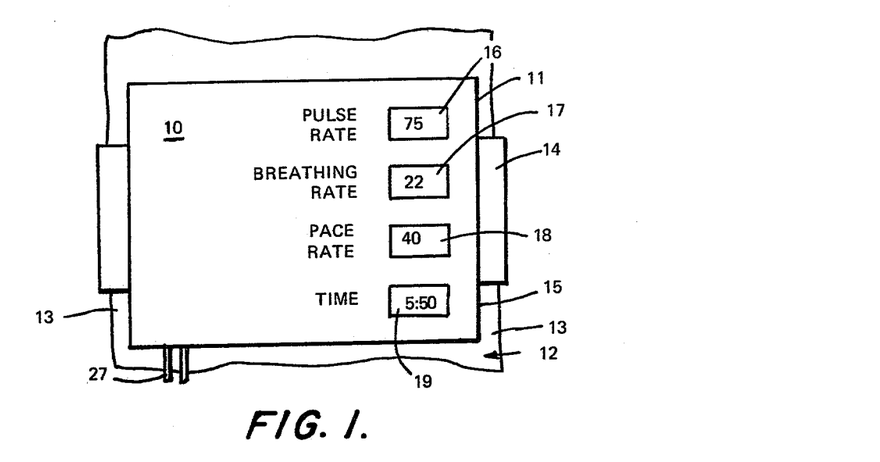
FIG. 1 is a perspective view of the indicating device attached to the wrist of the user.

As shown in FIG. 1 the invention is embodied in a device 10 comprising a case 11 attached to a wrist 12 in close proximity to the skin 13 by the strap 14. The case is generally rectangular in shape in the embodiment shown with the underside surface 15 configured to conform to the shape of the wearer's wrist. This case houses the electronic circuitry and readout systems for the invention.

As shown, a first display 16 indicates the "pulse rate" and is designated by those words printed thereby. Similarly a second display 17 shows the "breathing rate", while the "pace rate" is indicated in the display 18 and the "time" in the display 19. Preferably these displays are a low power digital type commonly used in wristwatches. Thus the jogger is afforded the opportunity of determining at a glance his present pulse or heartbeat rate, breathing rate and pace rate as well as the present time in this device. Such displays inform the jogger of the severity of the exercising by indicating the influence of that exercise on the body. The jogger is given a clear indication of not only his rate of exercise but from the time display, can determine the time duration of that exercise.

Figure 2:
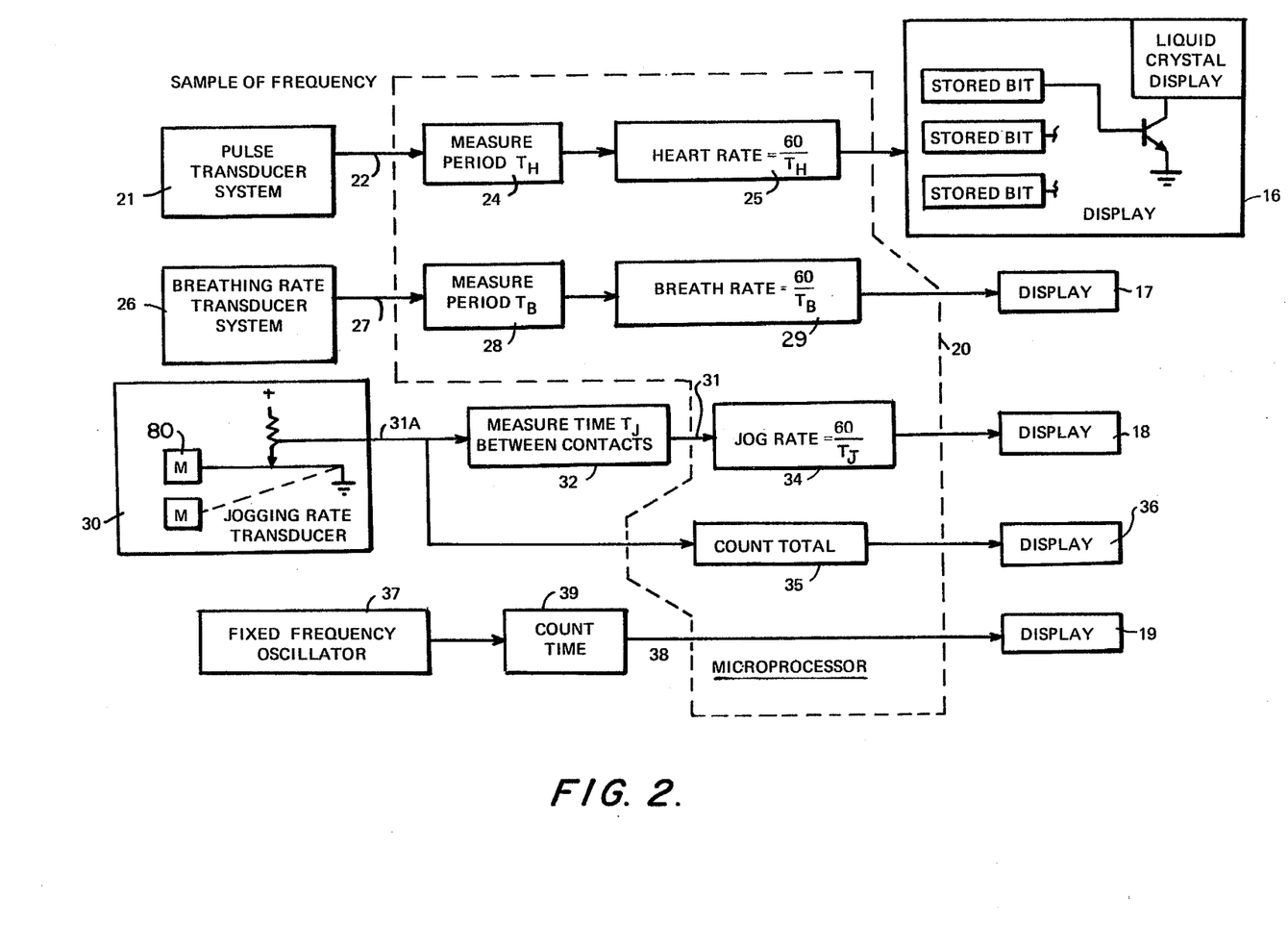
FIG. 2 shows a block diagram of the preferred circuit for the device of FIG. 1.

Illustrated in FIG. 2 is a block diagram showing the various functions which must be performed by the systems and circuitry for generating the displays described relative to FIG. 1. For instance the displays 16, 17, 18 and 19 are shown in diagrammatic form receiving signals from a circuit block 20. To generate the pulse rate shown in the display 16, there is provided a pulse transducer system 21 providing a signal through the conductor 22 which subsequently is processed by the circuit block to generate a time period for a pulse as indicated by the block 24, which time period subsequently is divided into the number sixty at block 25 to generate a signal indicative of the pulses per minute.

Similarly a breathing rate transducer 26 is provided which generates a signal transmitted through the conductor 27 and which is processed at the block 28 to generate a time period for each breathing cycle. This time period is subsequently divided into the number sixty as indicated by the clock 29 to supply to the display 17 a signal indicating a breathing rate per minute.

Figure 3:
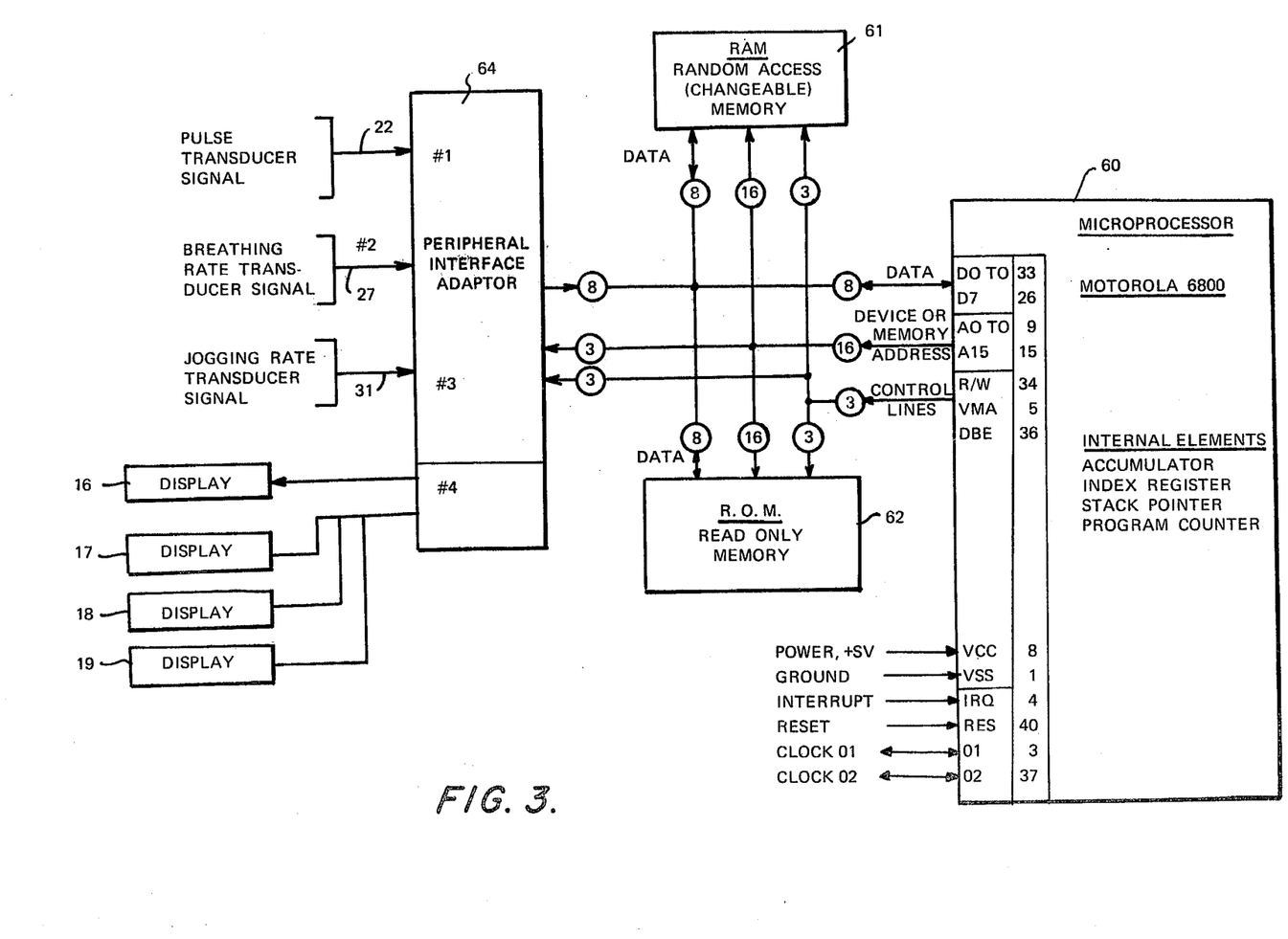
FIG. 3 shows a preferred circuit for the block diagram of FIG. 2.

A pace rate transducer 30 is provided which generates a signal supplied through the conductor 31A indicative of each pace to the block 32 for supplying a signal on conductor 31 indicating the time between paces which in turn is divided into the number sixty to obtain the number of steps per minute at the block 34 which signal is subsequently supplied to the display 18. In addition an alternative display can be provided which is not shown in FIG. 1 but which will include a total number of paces or steps determined by the counter 35 and displayed by a display 36. There is provided a fixed frequency oscillator 37 which generates a signal transmitted through the conductor 38 to a counter 39 for display of the time at the display 19. FIG. 3 shows an embodiment of circuit block 20 and will be discussed later.

Figure 4:
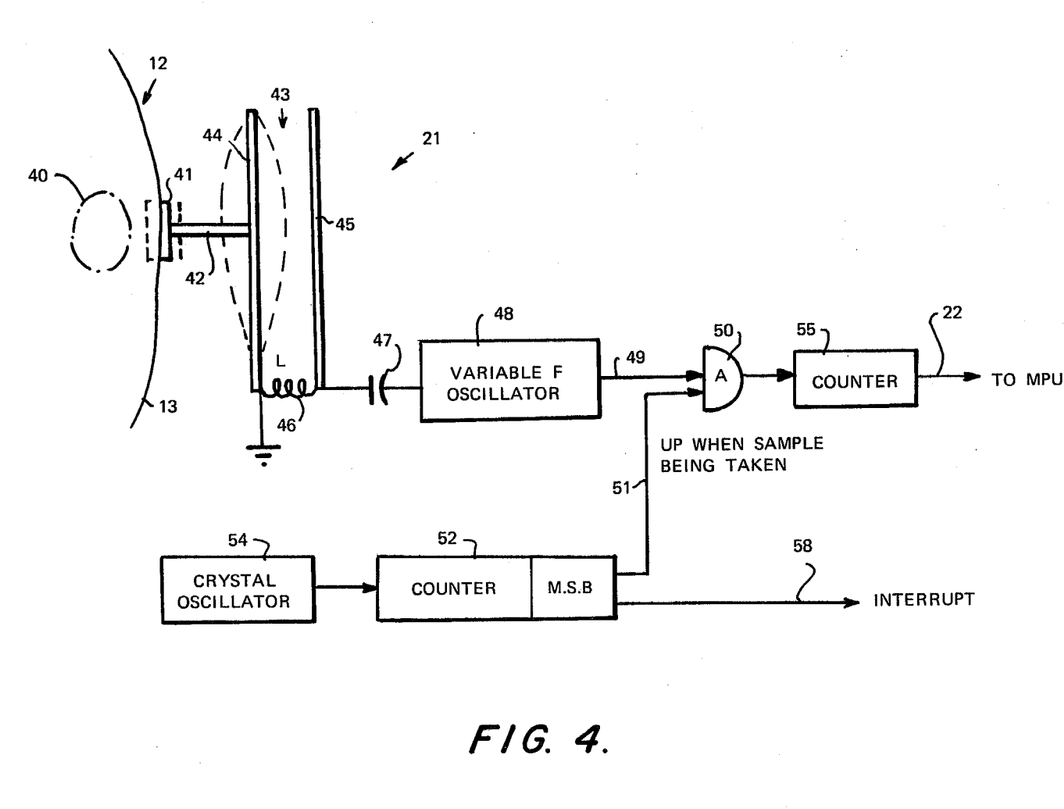
FIG. 4 is a block diagram of a system for detecting pulse rate.

An example of the pulse cycle transducer system 21 is shown in FIG. 4. This system is utilized to generate a first signal responsive to changes in contour of the wrist due to the blood pressure in the wrist changing with the pulse cycles of the wearer of the device. In this drawing the wrist 12 and skin 13 are shown in which the artery is represented by the dotted outline 40. Strapped adjacent the artery is a pad 41 having a connector 42 attached and extending to a plate 44 of a capacitor 43. Pad 41 is on the strap 14 or the case 15. The other plate 45 is fixed in position in the case 11 or on the strap 14 with an inductor 46 being electrically connected between the plates. These components along with the capacitor 47 form the tank circuit of a variable frequency oscillator 48. The tank circuit establishes the frequency of oscillation of this oscillator. This variable frequency signal is supplied through the conductor 49 to an AND gate 50.

Also supplied to the AND gate 50 is a periodic signal transmitted through the conductor 51 from a counter 52 supplied with a constant frequency signal from the crystal oscillator 54. In this manner, there is supplied to a counter 55 a periodic sampling of the signal from the variable frequency oscillator. It is important that such sampling occur several times for each expected pulse or heartbeat. Thus as shown in FIG. 6, the waveform 56 represents the values for a plurality of frequency signals 57, 57A and 57B each sampled upon the occurrence of a signal through the conductor 51 controlling the AND gate 50.

Figure 6:
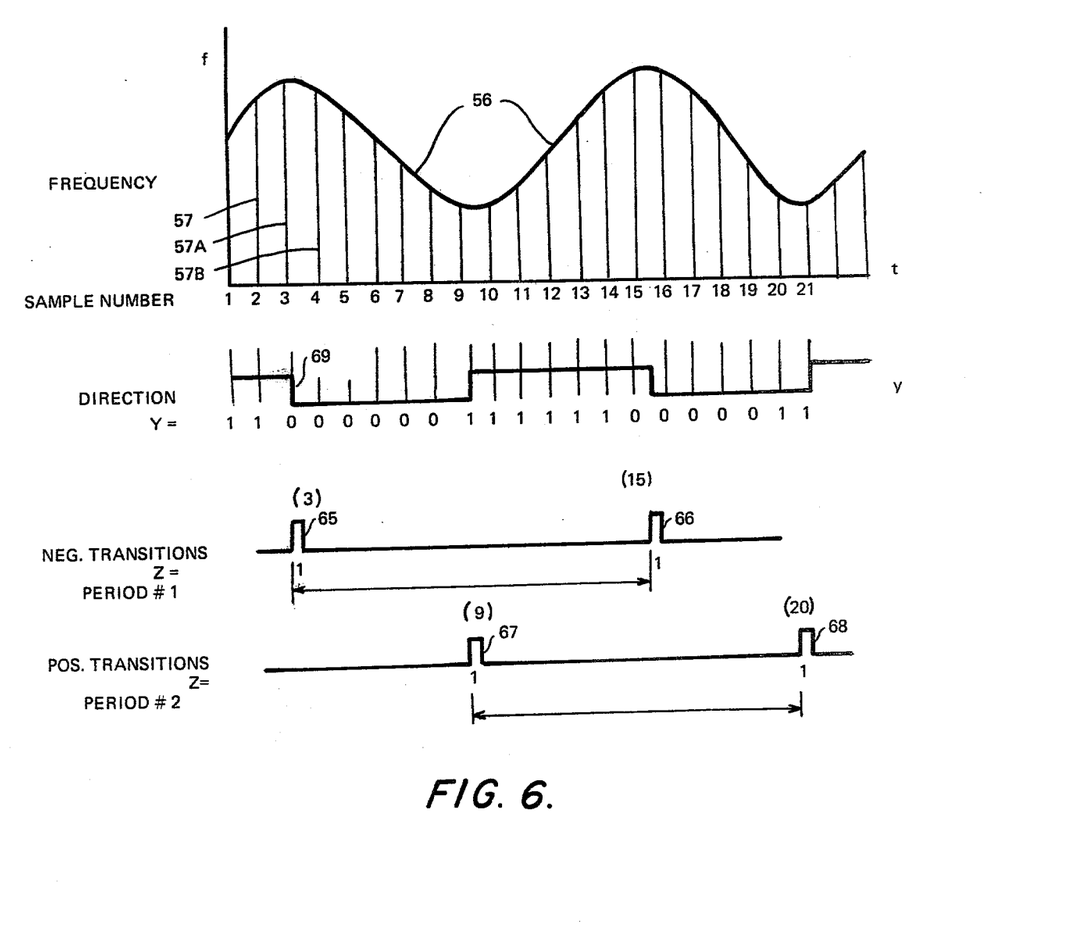
FIG. 6 shows representative waveforms for the circuits of FIGS. 4 and 5 and their programmed analysis.

Thus the counter 52 initiates the samples 1 through 21 shown in FIG. 6. The waveform 56 represents the variance in frequency due to changes in the capacitance of the capacitor 43 which in turn is responsive to movement of the plate 44 due to the pulse being sensed in the arm of the wearer. The frequency is indicated by the vertical length of each line in the drawing. The counter 55 changes this analogue frequency signal to digital form for subsequent processing as will be explained later.

Figure 7:
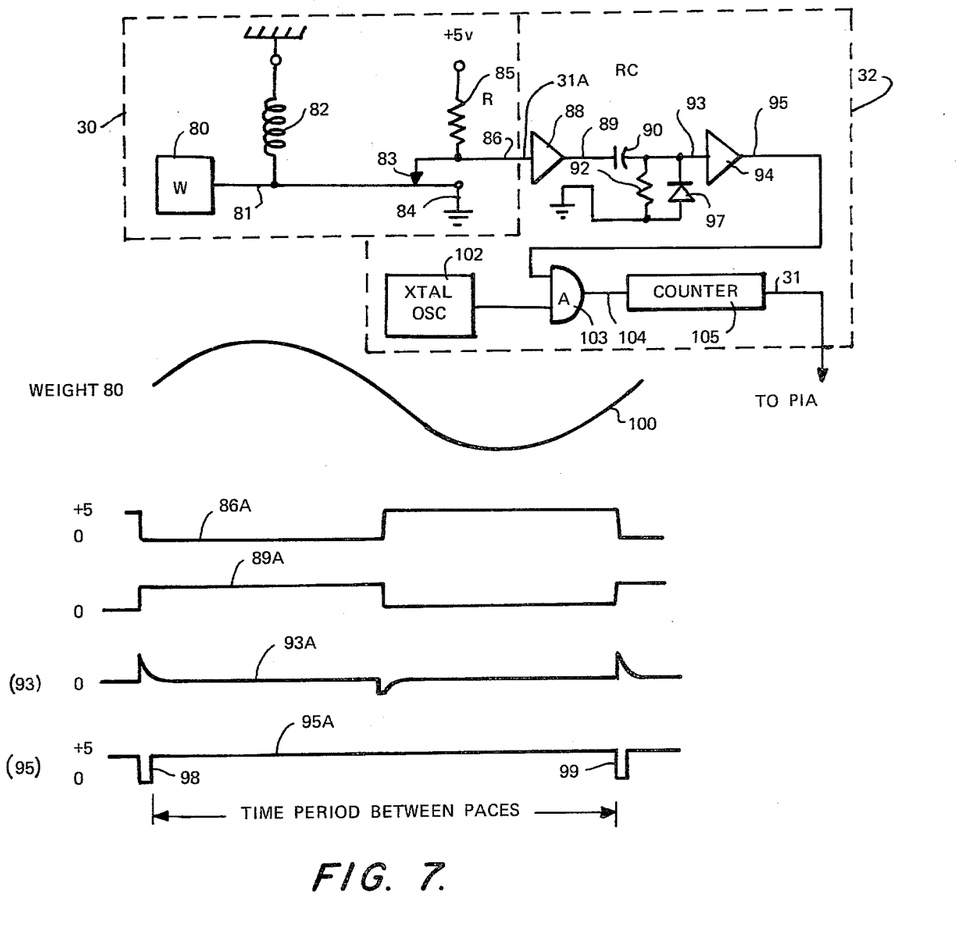
FIG. 7 is a block diagram with waveforms for detecting the pace rate.
Figure 8:
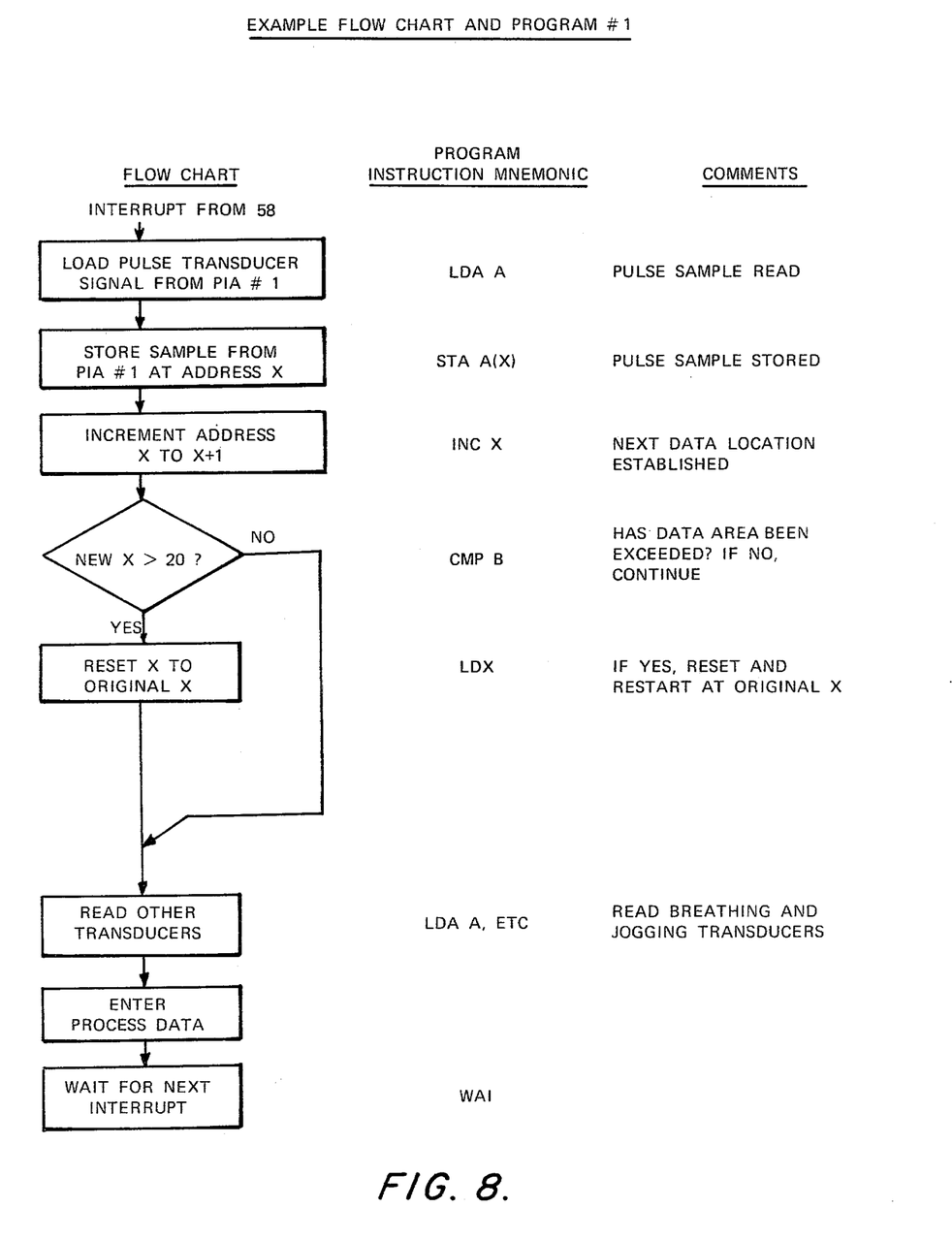
FIG. 8 is an example of a flow chart for a program for loading the pressure readings shown in FIG. 6 into the memory of FIG. 3.
Figure 9:
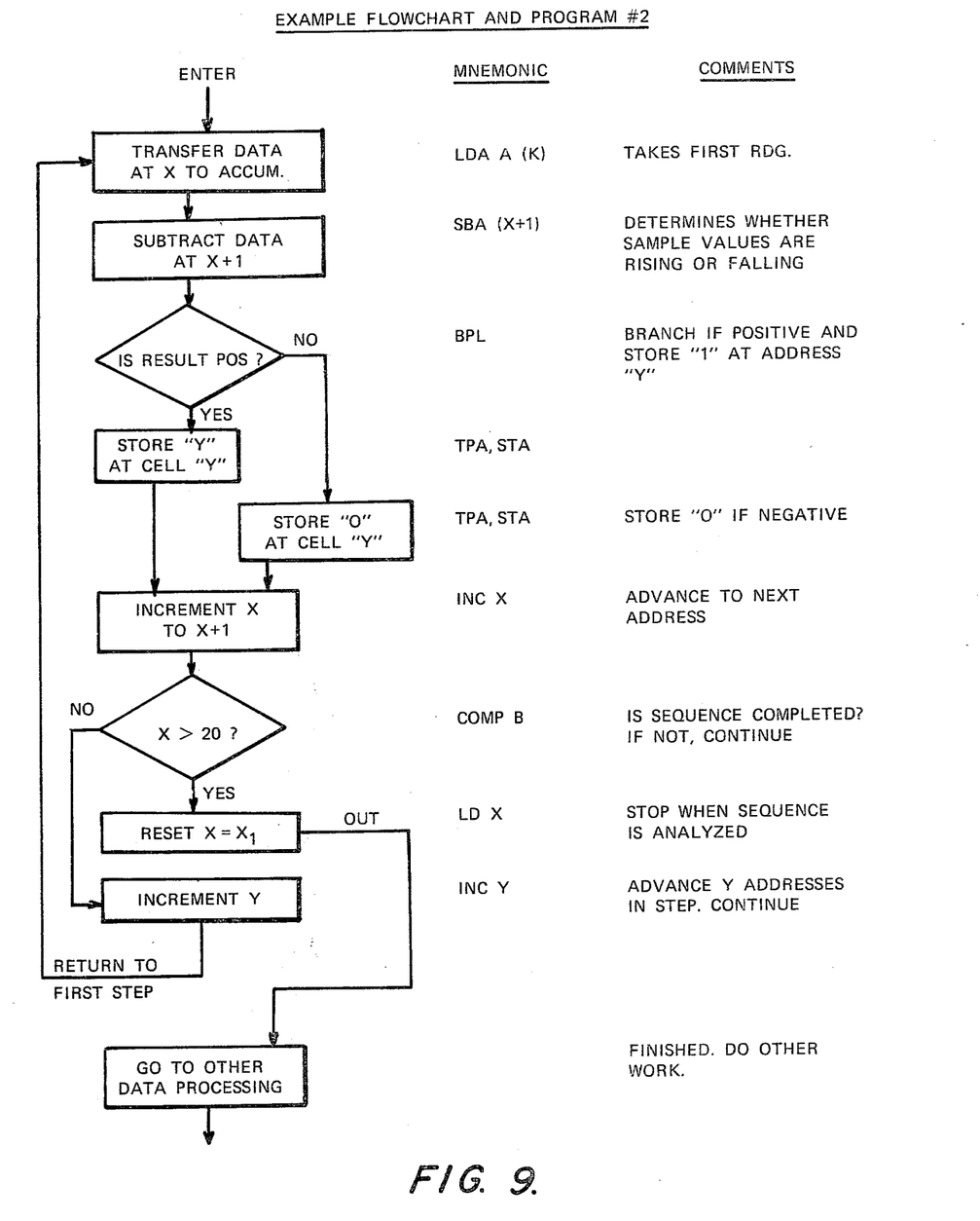
FIG. 9 is an example of a flow chart for an initial program for converting the pressure responsive signals obtained in the circuits of FIG. 4 and memory readings of FIG. 8 to a pulse rate.

The block 20 can be a microprocessor system which is programmed to receive these various signals and generate a display signal responsive thereto. One example of such a microprocessor is shown in FIG. 3 wherein the circuit is adapted for use with the Motorola * Microprocessor No. MC 6800. Associated with this microprocessor 60 is a Random Access Memory (RAM) 61 (Motorola MCM6810A) and a Read Only Memory (ROM) 62 (Motorola MCM6830A). In addition a Peripheral Interface Adapter (PIA) 64 (Motorola MC6820) is provided for receiving the transducer signals through the conductors 22, 27 and 31 and for supplying to the displays 16, 17, 18 and 19 the various signals indicating the body functions and the time. The various connections for such a microprocessor system are well-known to one skilled in the art and are also readily defined in the publications supplied by Motorola with the microprocessor. The Motorola Company supplies with the microprocessor the instructions for making all of the connections based on the various operations desired. Therefore the specific connections will not be discussed other than being shown in FIG. 3. The programming flow charts for the microprocessor to achieve the functions indicated in FIG. 2 are shown in FIGS. 7, 8 and 9. The derivation of the programs from the flow charts is a state of the art procedural step. Also other commercial circuits are available to perform the same functions and the Motorola circuits are shown only as a preferred embodiment.

*Trademark of Motorola Corporation

Figure 10:
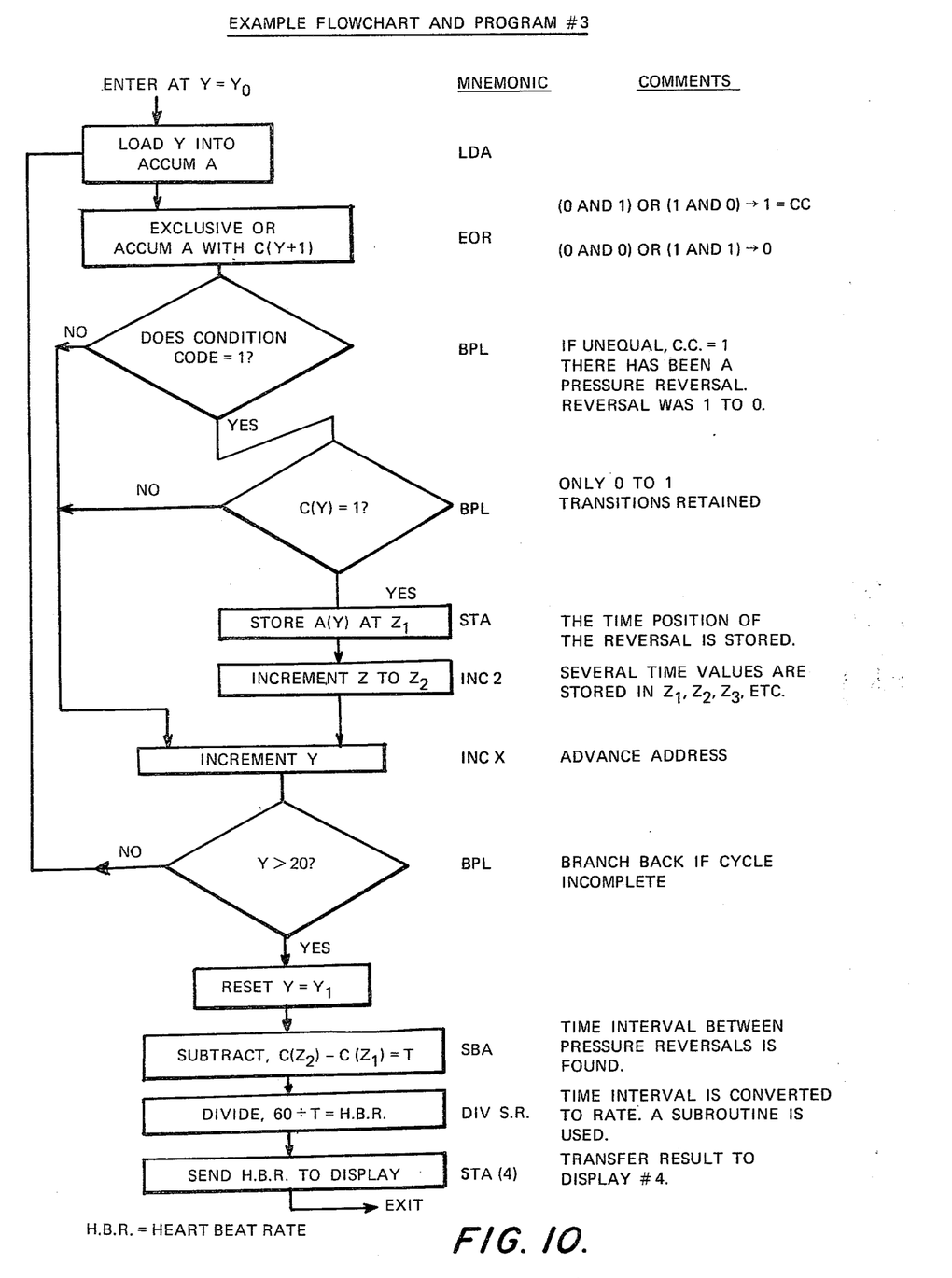
FIG. 10 is an example flow chart for a program for further converting the pressure responsive signals obtained in the circuits of FIG. 4 and flow chart of FIG. 9 to a pulse rate.

As shown in these FIGS. 8, 9 and 10, there is identified the flow chart, the program instruction and comments identifying the function being performed. Referring now to the flow chart an interrupt signal from counter 52 on line 58 starts the cycle. The first instruction transfers data from counter 55 via line 22 and via Peripheral Interface Adapter 64 (PIA) to the accumulator in MPU 60. The next instruction moves the data to address X. Thereafter the address is updated to X+1 and a decision is made each time as to whether or not the new address is greater than 20. Twenty is the number of samples selected to roughly approximate or exceed the time frame for a single heartbeat or pulse cycle. If the number is less than 20, there is no modification to the program. If the number is 20 or greater, the address counter is set to zero and the old memory addresses are used for new data.

At the end of the data transfer cycle but before a new interrupt is transmitted via line 58, the time is used to read other transducers and to process data in response to other transducer input signals.

Thereafter as indicated in FIG. 8, the data is recovered from the random access memory starting at the address X to perform the processing of the signals indicated in FIG. 6. As shown in that figure it is desired to generate a signal indicative of the duration of one time period for a heartbeat which time period is equal to the time period between the pulse 65 and the pulse 66 or the time period between the pulse 67 and the pulse 68. In order to obtain these pulses the samples 1 through 21 are obtained by use of the circuit of FIG. 4 and thereafter the output signal waveform 69 is generated which is a square wave with transitions occurring at each point of change in the sign of the slope of the waveform 56. The change in progression or sign of the slope indicates that an increasing pressure situation has changed to a decreasing pressure situation or vice-versa. By detecting the time increment between like occurrences, the duration of a pulse is indicated which time period is then utilized to calculate the number of pulses per minute.

Referring to FIG. 6, once again it is obvious from the curve 56 that the samples (3) and (15) relate to the highest pressure sensed by the capacitor 43. Thus these samples and the time periods they represent correspond with heartbeats or pulses because of the resulting higher pressure in the artery being sensed. Accordingly the generation of the time duration between these two samples corresponds to the time duration between heartbeats or the time period for one heartbeat and that quantity can be used to calculate the pulse rate per minute or the heartbeat rate.

In order to generate the waveform 69, the flow chart of FIG. 9 is utilized wherein the data is transferred from the first address X to the accumulator, thereafter the data at the adress X+1 is transferred and subtracted therefrom. If the result is positive a logical 1 is stored at a preselected address such as cell Y and if the result is negative, a logical 0 is stored at a cell Y. Thereafter the address X is incremented to X+1 and the sequence is repeated until X is greater than 20. The Y addresses are incremented in a manner equal to the incrementing of the X addresses. Twenty is an arbitrary choice corresponding to a number of samples extending over a sufficient time duration to encompass the slowest heartbeat rate expected to be sensed. Each time a calculation is made on a sample, a "1" or a "0" is stored corresponding to the "1"' and "0"' listed beneath a waveform 69.

Thereafter the flow chart of FIG. 10 is utilized to generate the pulse rate wherein the data at cell Y is loaded into an accumulator A and the result is exclusive OR combined with the data from cell Y+1 to detect the change, i.e. whether the slope is changing from negative to positive (0 to 1), or whether the slope is changing from positive to negative (1 to 0). Such a detection is necessary to determine corresponding points on the waveform 56 so that actual time durations between like transitions on the curve are detected. Thus a 1 indicates a negative-to-positive slope change and a 0 from the exclusive/or indicates no slope change. The program increments to compare the next two logical numbers from the various values in the cells Y. The results of each comparision are stored at cells $Z_1$ to $Z_{20}$ for negative-to-positive slope changes. In this example program positive-to-negative slope changes are deleted.

This sequence of steps is continued until 20 samples (or a preselected number) are recovered from cells Y and thereafter is repeated at the next sequence. The addresses of the pressure reversal points or transitions are stored in cells Z and are 65, 66 (negative) and 67, 68 (positive). Each Z cell contents represents a time interval. Subtracting two Z contents gives the time interval in seconds between pressure reversals. That time interval is then divided into 60 to determine the pulse rate per minute. The resulting signal is transmitted back to the peripheral interface adapter 64 for transmittal to the display 16. In addition the results are transmitted to the memory 61 so the signal is maintained on the display until the next calculation of pulse rate is made by repeat of the foregoing sequence. A more sophisticated program can be written which will reject false pressure changes.

Figure 5:
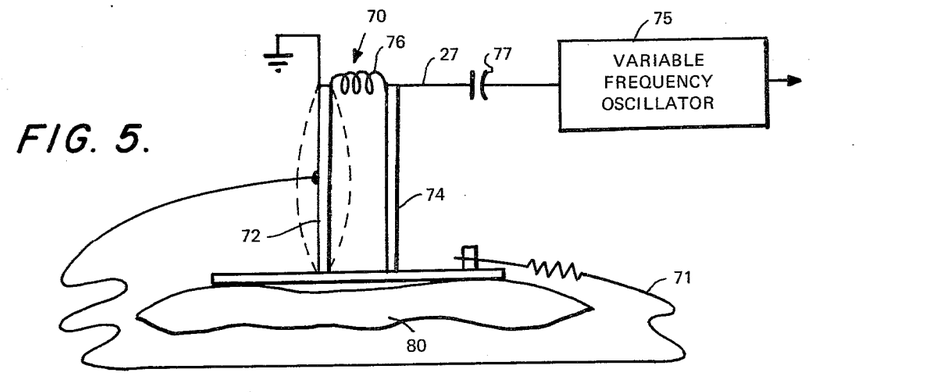
FIG. 5 is a block diagram of a system for detecting the breathing rate.

The breathing rate is detected in the manner illustrated in FIG. 5 wherein a capacitor assembly 70 is incorporated in a belt 71 which is strapped about the chest 80. It can be seen that with expansion of the chest, the capacitor plates 72 and 74 are moved relative to each other by varying tension on 71 to vary the capacitance between 72 and 74 thereby indicating that a breath is being taken. This capacitor 70 is connected into a circuit identical to that in FIG. 4 with the substitution of the capacitor 70 for the capacitor 43 in that circuit to form a tank circuit controlling the frequency of a variable frequency oscillator 75. The oscillator is of the same type as the oscillator 48 and the components including the inductor 76 and capacitor 77 function in the same manner to generate a second signal or waveform similar to that of waveform 56 in FIG. 6 indicating a breathing rate instead of a pulse rate. Since the operation of the microprocessor and the calculations for the breathing rate are substantially identical to that for detecting the pulse rate, this calculation sequence is not repeated.

To detect the jogging rate, it is well-known that as the foot strikes the ground there is a detectable jarring of the body. Also, the arms swing in exact synchronism with the legs. For this purpose in FIG. 7 a mass or weight 80 preferably supported on the body trunk of the wearer or within the device itself is utilized in the jogging or pace rate transducer 30, which weight is suspended on the end of a spring arm 81—which in turn is anchored at the opposite end 84 and is spring loaded by the spring 82. Thus a contact 83 is opened and closed at the rate the feet are set on the ground and this signal is fed through the conductor 31 comprising a series of pulses.

To generate this pulse signal the signal 86A in the conductor 86 is fed through an isolation amplifier 88 to generate the signal 89A transmitted through the conductor 89. The conductor includes the d.c. isolation capacitor 90 for passing only the edges of signal 89A. Thereafter this square wave signal 89A is differentiated by capacitor 90 and the resistor 92, and with the diode 97 generates the pulse signal 93A which is transmitted through the conductor 93 to the amplifier 94 which transmits the resulting pulse signal 95A through the conductor 95 to the AND gate 103.

The third signal comprising the pulses 98 and 99 of the signal 95A represent like points on the sine wave 100 representing the cyclic movement of the weight 80. Thus the time period between these pulses is the time period for one pace of the wearer. By supplying a constant frequency signal from the oscillator 102 to the AND gate 103 and counting the pulses transmitted through conductor 104 to the counter 105, the time period between paces is determined. That signal is supplied through the conductor 31 to the peripheral interface adaptor 64 as shown in FIG. 3. Thereafter this time period is divided into 60 and is displayed in the display 18 as a pace rate or the number of paces per minute being sensed.

The microprocessor also utilizes the fixed frequency oscillator 102 to supply a repetitive signal for the updating of the time display 19 (these means are not shown). Such circuits are state of the art in watch technology and will not be explained further. It should be understood further that while a specific embodiment of the invention is shown, alternate means for measuring the breathing rate could include a microphone and audio filter system, to hear the inhalation and exhalation sounds and convert these to a breathing rate, or a button to be pressed with each breath by the user and this period displayed as the breathing rate. From the foregoing it can be seen that the wearer of the subject device is provided with a constant display of the meaningful body functions most affected by the exercise.

The invention claimed is:

1. A device for measuring body conditions of the wearer, comprising in combination:
    means for sensing movement of the skin due to a body function;
    support means for attaching said movement sensing means in close proximity to a selected section of skin exhibiting movement indicating the manner of functioning of a portion of the wearer's body;
    a variable frequency oscillator circuit having a component acting in response to the skin movement sensing means for varying the output frequency signal of the circuit in response to movement of the skin;
    means for storing a plurality of successive samples of said output frequency signal; and
    means for detecting and indicating when the frequency signal is increasing and decreasing in frequency by by detecting the polarity of the difference in frequency between adjacent samples of said output frequency signal to detect cycles of the body function being detected thereby to indicate the manner of functioning of the wearer's body.

2. A device for measuring body conditions of the wearer, comprising in combination:
    means for sensing movement of the skin due to pulse cycles in a wrist, comprising a capacitor having two plates, with one plate adapted to be mounted stationarily on the wrist and the other plate adapted to be mounted adjacent the wrist for movement with the skin as the pulse cycles vary the contour of the wrist;
    means for attaching said skin movement sensing means on the wrist;

means for generating a first signal responsive to a change in capacitance of said capacitor, comprising a variable frequency oscillator having a tank circuit, said capacitor being connected in said tank circuit whereby the change in capacitance changes the oscillator output frequency to produce said first signal as an indication of pulse cycling;

means for determining the pulse cyclic rate from said first signal comprising means for sampling said first signal periodically within a pulse cycle, and means for comparing each sample of said first signal with the next sampled first signal to thereby detect cyclic changes in the frequency of said first signal representative of pulse cycling, and for generating output signals indicating a change in the progression of the frequency changes in the first signal; and means responsive to said output signals for indicating the pulse cyclic rate to the wearer.

3. A device as defined in claim 2 wherein said means responsive to said output signals indicates visually the pulse cyclic rate.

* * * * *